(12) United States Patent
Chow

(10) Patent No.: US 11,953,760 B2
(45) Date of Patent: Apr. 9, 2024

(54) METHODS OF DESIGNING REVERSE GEOMETRY LENSES FOR MYOPIA CONTROL

(71) Applicant: Edward Chow, North York (CA)

(72) Inventor: Edward Chow, North York (CA)

(73) Assignee: Edward Chow, North York, CA (US)

( * ) Notice: Subject to any disclaimer, the term of this patent is extended or adjusted under 35 U.S.C. 154(b) by 0 days.

(21) Appl. No.: 17/895,514

(22) Filed: Aug. 25, 2022

(65) Prior Publication Data
US 2023/0204977 A1 Jun. 29, 2023

Related U.S. Application Data

(63) Continuation of application No. 16/827,522, filed on Mar. 23, 2020, now Pat. No. 11,460,718, which is a
(Continued)

(51) Int. Cl.
*G02C 7/04* (2006.01)
*A61B 3/00* (2006.01)
(Continued)

(52) U.S. Cl.
CPC ............ *G02C 7/047* (2013.01); *A61B 3/0025* (2013.01); *A61B 3/1005* (2013.01); *A61B 3/103* (2013.01);
(Continued)

(58) Field of Classification Search
CPC ........ G02C 7/047; G02C 7/027; G02C 7/049; G02C 2202/24; A61B 3/0025; A61B 3/1005; A61B 3/103; A61B 3/107
(Continued)

(56) References Cited

U.S. PATENT DOCUMENTS

| 10,001,660 B1 * | 6/2018 | Chow | ................. | A61B 3/103 |
| 10,598,956 B2 * | 3/2020 | Chow | ................. | A61B 3/107 |

\* cited by examiner

*Primary Examiner* — Mohammed A Hasan

(57) ABSTRACT

Generating an aspheric contact lens design for facilitating myopia control of a cornea of a patient includes operations of: obtain measurement for degree refractive error of the eye in diopters; obtain measurement of one or more biomechanical properties of the cornea; define a diameter of a central zone of the contact lens based on pupil size; select a base curve profile and width for the central zone based on the refractive error and the one or more biomechanical properties; define a width of a reverse zone adjacent to and encircling the central zone, the width being greater than 0.5 mm; select a reverse curve profile for the reverse zone compatible with the base curve profile; modify the base curve profile adjacent to the reverse zone by applying a selected base eccentricity curve profile for enhancing the tension force strength of the reverse zone; define a width of a relief zone of the contact lens adjacent to and encircling the reverse zone; select a relief curve profile for the relief zone; define a width of an alignment zone of the contact lens adjacent to and encircling the relief zone; select an alignment curve profile for the alignment zone; and define a width of a peripheral zone of the contact lens adjacent to and encircling the alignment zone; select a peripheral curve profile for the peripheral zone; wherein the compression force strength and the tension force strength of the contact lens cooperate to reshape corneal curvature in a mid-peripheral region to address the myopia control when the contact lens is applied to the eye.

16 Claims, 8 Drawing Sheets

Related U.S. Application Data continuation of application No. 15/988,079, filed on May 24, 2018, now Pat. No. 10,598,956, which is a continuation of application No. 15/441,763, filed on Feb. 24, 2017, now Pat. No. 10,001,660.

(51) Int. Cl.
*A61B 3/10* (2006.01)
*A61B 3/103* (2006.01)
*A61B 3/107* (2006.01)
*G02C 7/02* (2006.01)

(52) U.S. Cl.
CPC .............. *A61B 3/107* (2013.01); *G02C 7/027* (2013.01); *G02C 7/049* (2013.01); *G02C 2202/24* (2013.01)

(58) Field of Classification Search
USPC .................................................. 351/159.23
See application file for complete search history.

METHODS OF DESIGNING REVERSE GEOMETRY LENSES FOR MYOPIA CONTROL

CROSS-REFERENCE TO RELATED APPLICATIONS

The present application is a continuation application of U.S. patent application Ser. No. 16/827,522, filed on Mar. 23, 2020, which is a continuation application of U.S. patent application Ser. No. 15/988,079, filed on May 24, 2018, which is a continuation application of U.S. patent application Ser. No. 15/441,763, filed on Feb. 24, 2017; the entire contents of which are hereby incorporated by reference herein.

FIELD

The present invention is related to contact lens design.

BACKGROUND

Near-sightedness, also known as short-sightedness or myopia, is a condition of the eye where light undesirably focuses in front of, instead of on, the retina. The improper positioning of the light focus has undesirable vision consequences, as distant objects appear blurry while close objects appear more normal. Experiencing blurry images can manifest as headaches and eye strain. It is known for severe near-sightedness, increase in risk of retinal detachment, cataracts, and glaucoma can be experienced by the person. The underlying mechanism of myopia involves the length of the eyeball being too long or less commonly the lens being too strong, and as such can be characterized as a type of refractive error.

Myopia can be corrected with eyeglasses, contact lenses, or surgery, however such correction is short-lived as the degree of myopia for a person's eyeball can increase over time, thus requiring changes to their prescription eyeglasses and contact lenses. As surgery does not prevent the progression of myopia, additional surgeries may be required if myopia continues to develop. As such, eyeglasses are the easiest and safest method of correction, eyeglasses are only a temporary corrective measure and therefore do not provide for myopia control, i.e. inhibiting the progression of myopia (e.g. continual lengthening of the person's eyeball over time). Contact lenses can provide for myopia control (to some degrees depending on the design of the lens) as well for myopia correction. The chance of myopia control may be limited with various degree of success depending on the formats used. However, all kinds of contact lenses may associate with a risk of infection due to close contact with the corneal surface during application, which causes abrasion and scratching of the cornea eyeball. A properly designed lens may reduce these risks. Refractive surgery can permanently change the shape of the cornea; however this type of correction suffers the same disadvantages as eyeglasses when it comes to the lack of effective myopia control. Orthokeratology or overnight corneal reshaping uses the forces created under specially designed reverse geometry GP (gas permeable) lenses, or molds, to temporarily change corneal shape for myopia reduction (correction). Normal vision can be achieved during the entire day with long term myopia controlling effect.

In terms of contact lenses for myopia control, a treatment zone (of the contact lens) applies suction to the eyeball in order to reform the eyeball shape and thus decrease the length of the eyeball. However, the treatment zone needs to have an increased strength for higher levels of myopia, however this also causes a disadvantage of the suction force being too great and thus causes the contact lens to contact the surface of the eyeball and become stuck or otherwise attached thereon. In extreme examples, it has been observed that a high myopia lens creates an audible popping sound when removed from the eyeball, clear evidence of lens adhesion to the eyeball surface. Contact with the eyeball needs to be avoided, as this contact contributes to abrasion of the eyeball surface tissues as the lens moves about the eyeball during eye movement (e.g. during REM—rapid eye movement), as well as when the lens is applied or removed with respect to the eyeball. Known examples of lens types applied to myopia for orthokeratology are spherical and toric, however both of these lens types suffer from the disadvantage stated above for higher levels of myopia, i.e. increased risk and occurrence of lens adhesion to the eyeball surface. Current state for the art for myopia lenses dictates that increasing suction levels are accomplished via decreasing the width of the fitting zone, however decreased widths cannot accommodate for manufacturing tolerances/errors of the lens material as well as ability for the eyeball tissue to react (i.e. deform) properly to the applied suction forces. On the contrary, increased widths of the fitting zone can provide room for the eyeball tissue to react properly to the applied suction forces, as well as to inhibit manufacturing tolerances/errors of the lens material. However increasing the fitting zone width has the undesirable consequence of reducing the strength of the suction force and thus making the lens ineffective for treating myopia for higher diopter values.

SUMMARY

An object of the present invention is to provide a lens design method and system to obviate or mitigate at least one of the above-presented disadvantages.

A first aspect provided is a method for generating an aspheric contact lens design for facilitating myopia control of a cornea of a patient, the method stored as a set of instructions in memory for execution by a computer processor to: obtain measurement for degree refractive error of the eye in diopters; obtain measurement of one or more biomechanical properties of the cornea; define a diameter of a central zone of the contact lens based on pupil size, the diameter being equal to or less than a selected dimension; select a base curve profile and width for the central zone based on the refractive error and the one or more biomechanical properties, the base curve profile defining a compression force strength on the cornea when the contact lens is positioned on the eye, the base curve profile including a central zone tear layer thickness and a central zone radius of curvature; define a width of a reverse zone adjacent to and encircling the central zone, the width being greater than 0.5 mm; select a reverse curve profile for the reverse zone compatible with the base curve profile, the reverse curve profile defining a tension force strength on the cornea when the contact lens is positioned on the eye, the reverse curve profile including a reverse zone tear layer thickness and a reverse zone radius of curvature; modify the base curve profile adjacent to the reverse zone by applying a selected base eccentricity curve profile for enhancing the tension force strength of the reverse zone, said applying contributing to the aspheric nature of the contact lens, the base eccentricity curve profile including an aspheric zone tear layer thickness and an aspheric zone base eccentricity; define a width of a relief zone of the contact lens adjacent to and encircling the reverse zone; select a relief curve profile for the relief zone, the relief curve profile moderating the tension force strength adjacent to the relief zone, the relief curve profile including a relief zone tear layer thickness and a relief zone radius of curvature; define a width of an alignment zone of the contact lens adjacent to and encircling the relief zone; select an alignment curve profile for the alignment zone, the alignment curve profile including an alignment zone tear layer thickness and an alignment zone radius of curvature; and define a width of a peripheral zone of the contact lens adjacent to and encircling the alignment zone; select a peripheral curve profile for the peripheral zone, the peripheral curve profile including a peripheral zone tear layer thickness and a peripheral zone radius of curvature; wherein the compression force strength and the tension force strength of the contact lens cooperate to reshape corneal curvature in a mid-peripheral region to address the myopia control when the contact lens is applied to the eye.

A second aspect provided is a lens design machine for generating an aspheric contact lens design for facilitating myopia control of a cornea of a patient, the machine including: a measurement device for obtaining measurement for degree refractive error of the eye in diopters and for obtaining measurement of one or more biomechanical properties of the cornea; a computer processor and memory having a stored as a set of instructions for execution by a computer processor to: obtain measurement for degree refractive error of the eye in diopters; obtain measurement of one or more biomechanical properties of the cornea; define a diameter of a central zone of the contact lens based on pupil size, the diameter being equal to or less than a selected dimension; select a base curve profile and width for the central zone based on the refractive error and the one or more biomechanical properties, the base curve profile defining a compression force strength on the cornea when the contact lens is positioned on the eye, the base curve profile including a central zone tear layer thickness and a central zone radius of curvature; define a width of a reverse zone adjacent to and encircling the central zone, the width being greater than 0.5 mm; select a reverse curve profile for the reverse zone compatible with the base curve profile, the reverse curve profile defining a tension force strength on the cornea when the contact lens is positioned on the eye, the reverse curve profile including a reverse zone tear layer thickness and a reverse zone radius of curvature; modify the base curve profile adjacent to the reverse zone by applying a selected base eccentricity curve profile for enhancing the tension force strength of the reverse zone, said applying contributing to the aspheric nature of the contact lens, the base eccentricity curve profile including an aspheric zone tear layer thickness and an aspheric zone base eccentricity; define a width of a relief zone of the contact lens adjacent to and encircling the reverse zone; select a relief curve profile for the relief zone, the relief curve profile moderating the tension force strength adjacent to the relief zone, the relief curve profile including a relief zone tear layer thickness and a relief zone radius of curvature; define a width of an alignment zone of the contact lens adjacent to and encircling the relief zone; select an alignment curve profile for the alignment zone, the alignment curve profile including an alignment zone tear layer thickness and an alignment zone radius of curvature; and define a width of a peripheral zone of the contact lens adjacent to and encircling the alignment zone; select a peripheral curve profile for the peripheral zone, the peripheral curve profile including a peripheral zone tear layer thickness and a peripheral zone radius of curvature; wherein the compression force strength and the tension force strength of the contact lens cooperate to reshape corneal curvature in a mid-peripheral region to address the myopia control when the contact lens is applied to the eye.

BRIEF DESCRIPTION OF THE DRAWINGS

The foregoing and other aspects will be more readily appreciated having reference to the drawings, by way of example only, wherein.

DETAILED DESCRIPTION

Figure 6:
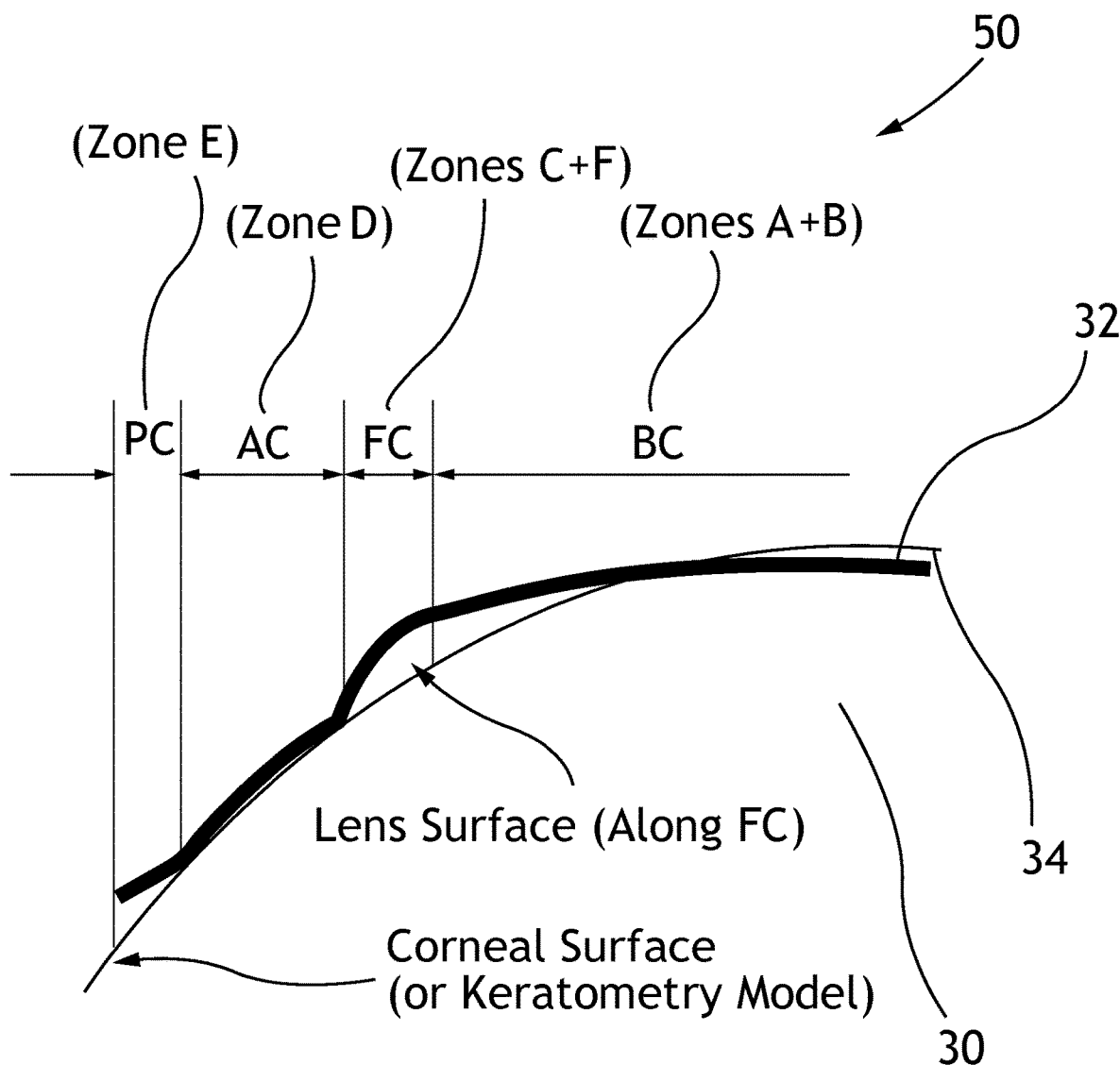
FIG. 6 shows an example positioning of the designed lens on a cornea of the system of FIG. 1.

Referring to FIG. 6, corneal changes created by wearing orthokeratology (ortho-k) lenses 32 are not mechanical; rather, they are created via fluid forces exerted under the various curves of the posterior lens surface with respect to the surface 34 of the eyeball 30. It is not a structural "bending" of the cornea surface 34, but rather a redistribution and relative thinning/thickening of the corneal epithelial cell layer due to forces exerted on the surface 34 as a result of wearing of the lens 32 over a period of time. The effects (i.e. redistribution of epithelial tissue) of ortho-k can be temporary, but can provide excellent visual acuity for 12 to 48 hours following lens 32 removal from the eye 30. The manipulation of the various curves of the posterior surface provides for a controlled and predictable change in the corneal topography that can result in improved unaided visual acuity (Controlled Clearance Philosophy). In addition, studies have shown that the effects of ortho-k can be completely reversible. Upon discontinuing ortho-k treatment, for effective myopia control, the refraction (Rx of the eyes) and topography could return to the baseline. After a desirable number of ongoing treatment periods, it is the refractive change of the corneal tissue, post application of the lens 32 (i.e. contributing to remolding of the corneal tissue as further explained below), that provides for myopia control.

Figure 1:
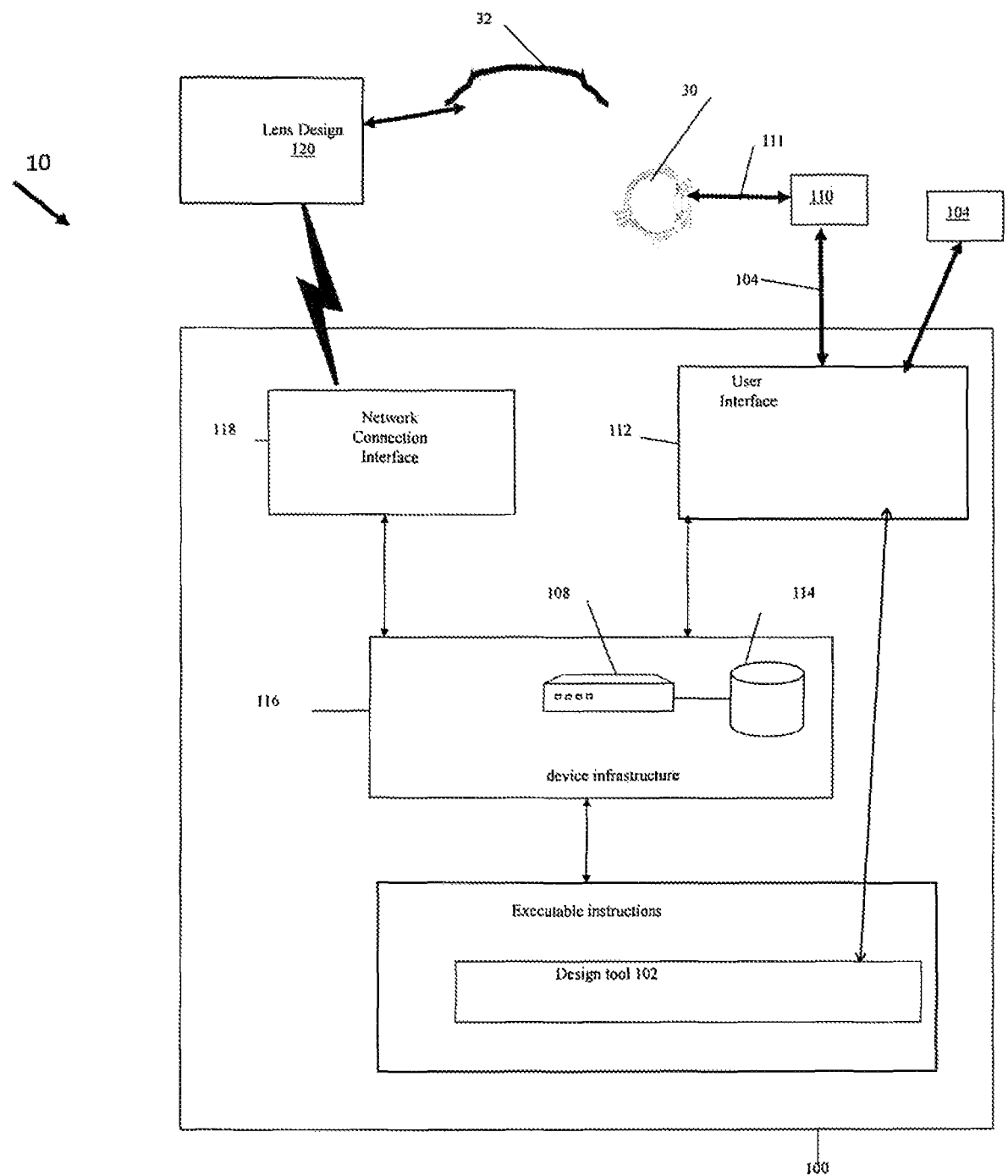
FIG. 1 is a view of a lens design system for designing a gas permeable contact lens for myopia control.

Referring to FIG. 1, shown is an illustrative lens design environment 10 having a computer device 100 for implementing a lens design tool 102 programmed via a set of lens design executable instructions stored in storage 114 of device infrastructure 116. The executable instructions of the design tool 102 are executed by a computer processor 108 of the device infrastructure 116. A user interface 112 of the computer device 100 is used to receive design parameters 104 provided by a user (e.g. optometrist) of the system 10. The design parameters 104 are chosen by the user based on patient eyeball 30 specifics (e.g. degree of myopia, corneal surface map, etc.). It is recognised that certain design parameters 104 can be measured and recorded by a corneal topographer 110, for example. An output of the design tool 102 is a lens design specification 120, specifying zone 50 (see FIG. 3) curve shape profiles and widths w, as well as tear film layer 36 thicknesses TLTi (see FIG. 4). From the lens design specification 120, a reverse geometry contact lens 32 can be manufactured for subsequent application to the patient's eye 30, in order to effect myopia control as further discussed below.

Figure 8:
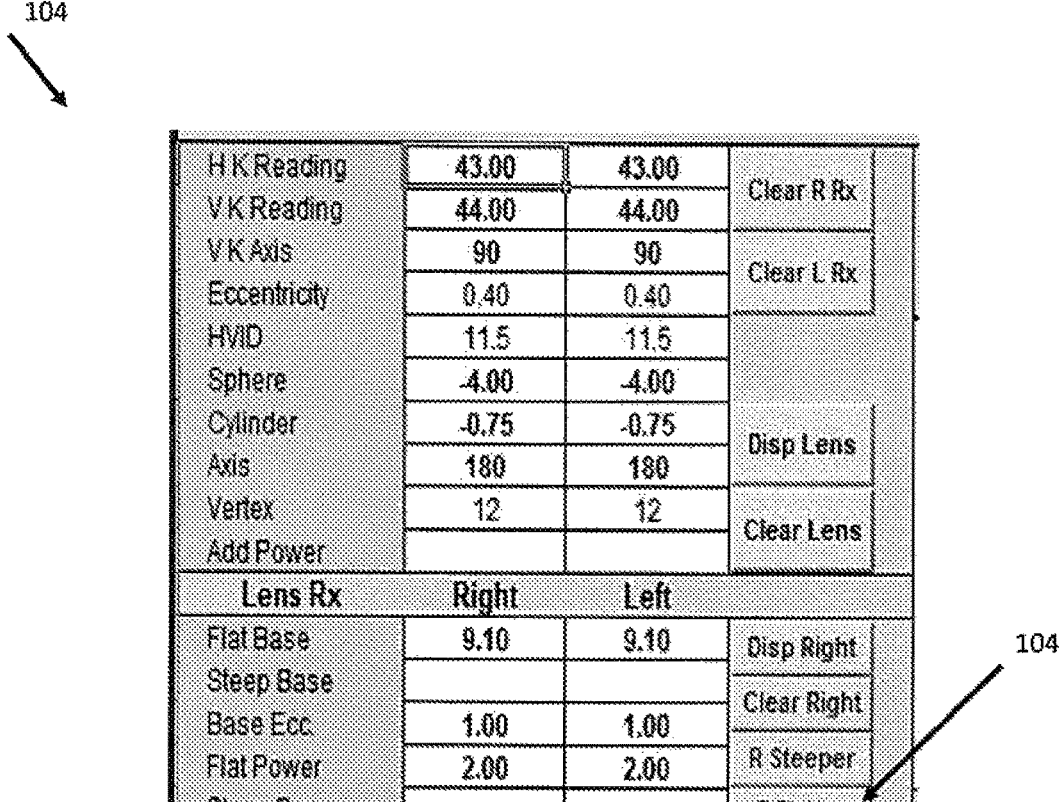
FIG. 8 shows example parameters of the tool of FIG. 1.

As further discussed below, the design parameters 104 used by the lens design tool 102 can include measurements of eye surface geometry (i.e. surface shape of the eyeball), as well as biomechanical properties of the eye such as viscosity and rigidity. An example machine 110 for measuring the eye surface geometry as well as the biomechanical properties could be an autorefractor or automated refractor as a computer-controlled machine used during an eye examination to provide an objective measurement of the eye for a person's refractive error and prescription for glasses or contact lenses. This can be achieved by measuring how light is changed as it enters a person's eye 30, repeated in at least three meridians of the eye 30 and the autorefractor calculates the refraction of the eye 30, sphere, cylinder and axis. Also, clinical devices 110, such as the Ocular Response Analyzer (ORA) or the Corneal Visualization Scheimpflug Technology (CorVis ST) can be used for measuring the corneal biomechanical properties of the eye 30, including corneal biomechanical parameters, axial length, and mean keratometry (i.e. K factor). Referring to FIG. 8, measured parameters 104 for each eye 30 (i.e. Right and Left) can be such as but not limited to: Horizontal and Vertical K readings related to Sphere diopter values (e.g. −4.00); Vertical K axis; eccentricity (recognising that a spherical eye curvature would have an eccentricity of 0); Horizontal Visible Iris Distance (HVID); and corneal diameter (which dictates the overall Diameter dimension of the lens 32). The machine 110 can include measurement devices 111 such as but not limited to Topographic based imaging measurement devices, air pressure generation devices, surface shape scanning devices, etc. It is recognized that the methodology of designing the lens 32 as described herein via tool 102 could be programmed and implemented in the machine 110, as desired.

Figure 7:
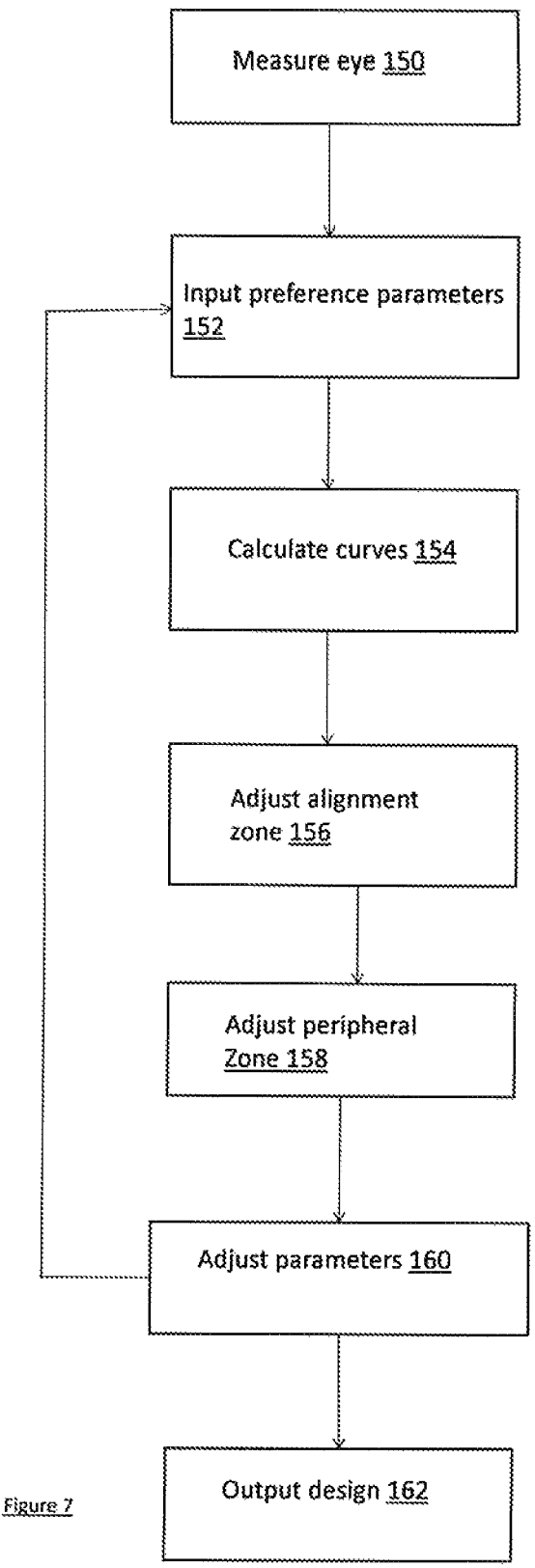
FIG. 7 shows an example operation of the lens design of FIG. 1.
Figure 9:
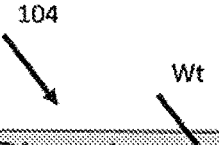
FIG. 9 shows further example parameters of the tool of FIG. 1.

As further described below, the steps associated with FIGS. 7, 8, 9 provide a particular solution to a problem or a particular way to achieve a desired outcome defined by the claimed invention, as opposed to merely claiming the idea of a solution or outcome. For example, the described steps define a specific way, namely use of particular rules as implemented via the executable instructions of the device(s) 100, 110 to obtain parameters 104 (measured or otherwise) to define overall dimensions and prescribed correction through defined zone widths and curve profiles (e.g. curve radii) along with tear layer thickness TLT to solve the problem of producing an appropriate lens design of desired corrective strength by forcing the width of the reverse zone to be greater than 0.5 mm while at the same time adjusting for decreases in corrective strength introduced by the reverse zone width being greater than 0.5 mm. It is recognised that conventional process is to increase the corrective strength of the lens by selecting narrower and narrower reverse zone widths, such that increasing of corrective strength is directly related to a decreasing of reverse zone width (i.e. less than 0.6 mm). Contrary to state of the art thinking, the presently described lens design via the tool 102 uses the defined rules to generate increased corrective strength of the lens via selecting reverse zone widths greater than 0.5 mm (e.g. 0.6 mm or greater due to 0.1 mm manufacturing increment limits) while at the same time selecting higher levels of base curve eccentric in the central zone (a or A and B) and relief zone F, as further described below.

It is recognised that lower viscosity and higher rigidity corneal tissue of certain patients (with respect to a population norm) provides for a reduced or delayed response to corneal tissue remolding facilitated by wearing of the designed lens 32. A further design parameter 104 supplied to the design tool 102 is the myopia degree for the measured eye 30. It is recognised that myopia, like all refractive errors, is measured in diopters (D), which are the same units used to measure the optical power of eyeglasses and contact lenses. Lens powers that correct myopia are preceded by a minus sign (−), and are usually measured in 0.25 D increments. The severity of nearsightedness is often categorized like this: Mild myopia: −0.25 to −3.00 D; Moderate myopia: −3.25 to −6.00 D; High myopia: greater than −6.00 D. Further design parameters 14 can include prescription Rx, preoperative keratology K value readings, central corneal thickness (CCT), edge thickness (ET) & pupil size, which can affect the overall diameter of the lens 32 as well as selected curve profile shapes of the zones 50 (see FIG. 3) and their corresponding widths w. It is recognised that the diameter of the base optical treatment zone (zones A+B) can be 6.0 mm or smaller and can be as small as 5.0 mm depending on the pupil size & the amount of targeting. Preferably the base optical treatment zone is 5.4 mm.

Figure 2:
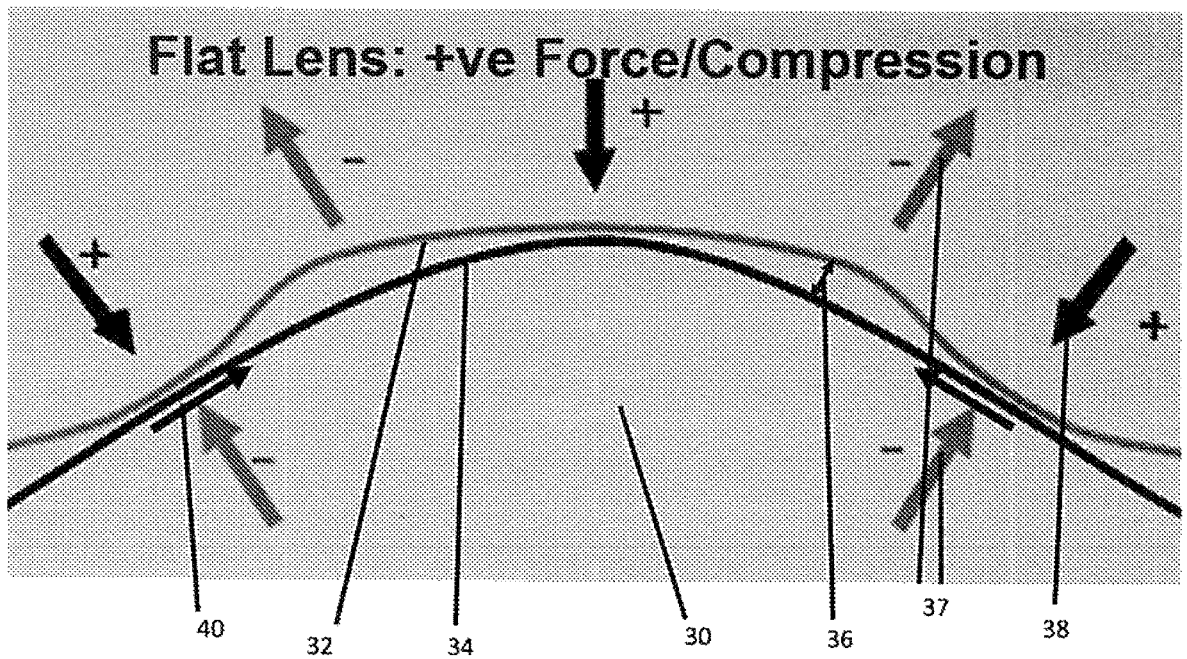
FIG. 2 is an illustrative force diagram of the lens of the system of FIG. 1.
Figure 3:
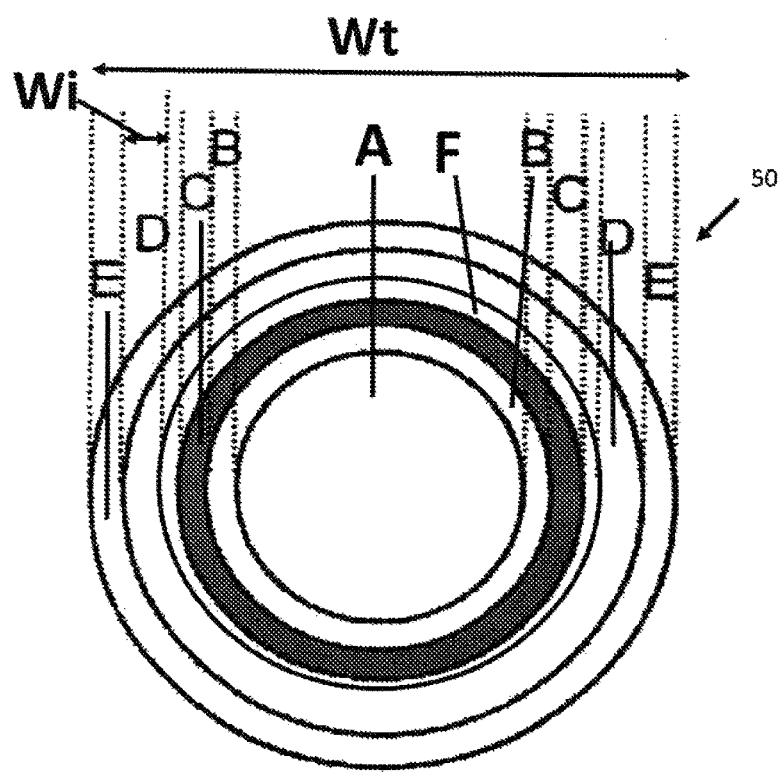
FIG. 3 shows example zones of the lens of the system of FIG. 1.
Figure 4:
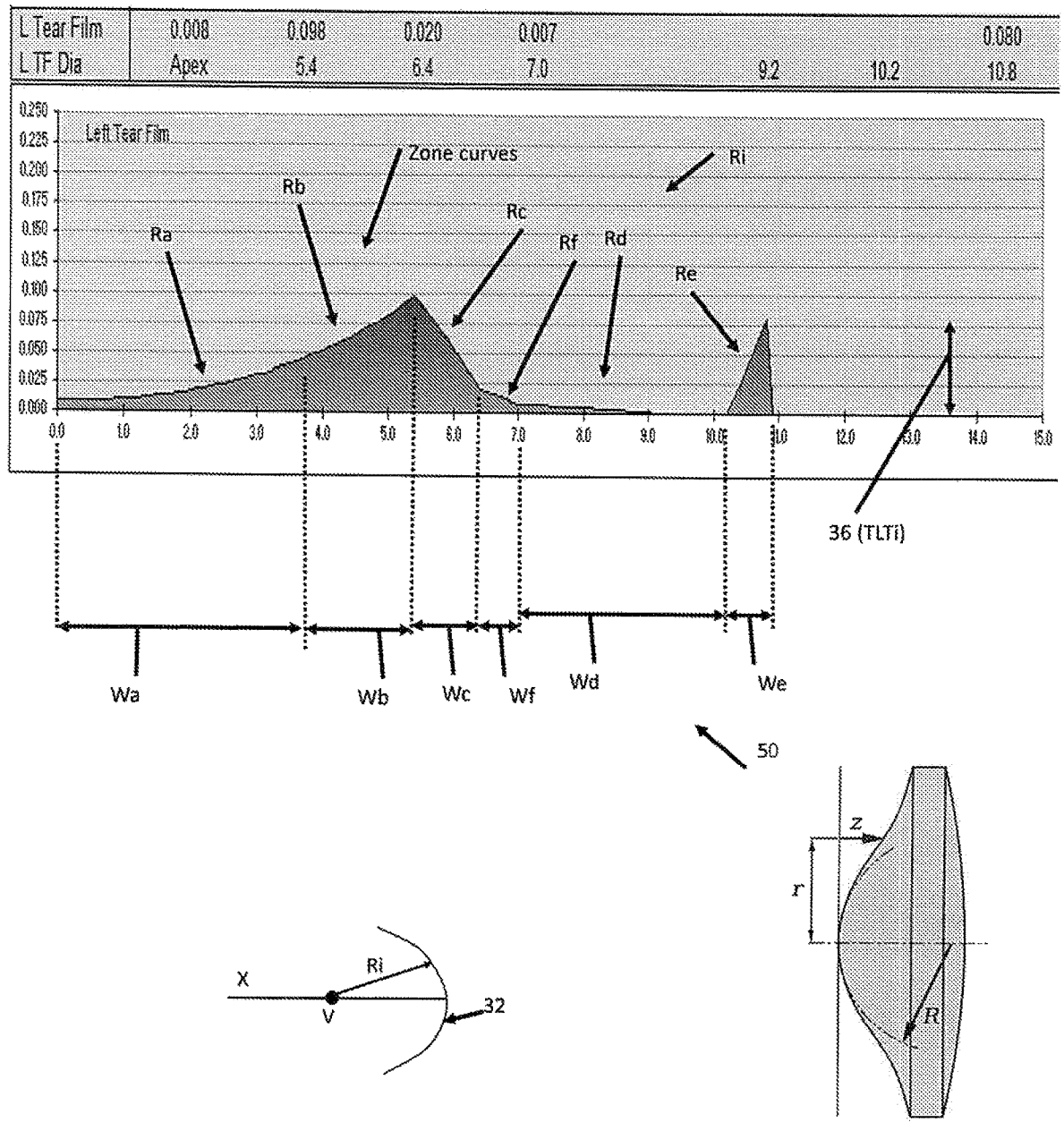
FIG. 4 shows an example configuration of the lens of the system of FIG. 1.

Referring to FIGS. 2, 3 and 4, contact lens 32 size is dictated by the size (i.e. diameter) of the person's eyeball 30, thereby for myopia control the available area for treatment, i.e. location of suction forces, is dictated by the overall size of the treatment zone (zones A and B and C and F) which leaves available space for the rest of the zones (e.g. alignment zone D, peripheral zone E, etc.). It is also recognised that the strength (i.e. steepness) of a reverse curve in the reverse zone C provides for the suction or tension force applied to the eye surface 34 of the person, for a given base curve of the central zone A (providing the compression force) and a given alignment curve of the alignment zone D (providing for maintaining positioning or alignment of the lens on the eyeball). As such, the width of the reverse zone C typically dictates the strength of the tension force permissible, such that narrower widths (e.g. less than 0.6 mm such as 0.5 mm) result in the creation of higher respective tension forces for a given reverse curve shape. As provided below, an alternative to using narrow width fitting zones (i.e. less than 0.6 mm) to generate increased tension forces, the present invention uses wider reverse zones C (e.g. 0.6 mm or greater tending to decrease/lower the tension force in the reverse zone C) which is then compensated for by 1) the application of a base eccentricity curve shape to the base curve shape in the central aspheric zone B adjacent to the reverse zone C and 2) the addition of a relief zone F with relief curve shape situated between the reverse zone C and the alignment zone D. The contribution of the application of the base eccentricity curve shape is to increase the tension force generated by the reverse curve via the introduction of the aspheric nature to the base curve shape (which is spherical in nature). At the same time, the addition of the relief zone F with associated relief curve shape provides for a reduction in the tension force experienced by the eye 30 in the reverse zone C adjacent to the relief zone F.

Further to the above, based on manufacturing tolerances such that the zone width increments are provided in 0.1 mm increments, the reverse zone C width Wc should be greater than 0.5 mm, e.g. 0.6 mm if only 0.1 increments are provided for during lens manufacturing. In this case, as provided below, an alternative to using narrow width fitting zones (i.e. less than or equal to 0.5 mm) to generate increased tension forces, the present invention uses wider reverse zones C (e.g. greater than 0.5 mm tending to decrease/lower the tension force) which is then compensated for by 1) the application of a base eccentricity curve shape to the base curve shape in the central aspheric zone B adjacent to the reverse zone C and 2) the addition of a relief zone F with relief curve shape situated between the reverse zone C and the alignment zone D. The contribution of the application of the base eccentricity curve shape is to increase the tension force generated by the reverse curve via the introduction of the aspheric nature to the base curve shape (which is spherical in nature). At the same time, the addition of the relief zone F with associated relief curve shape provides for a reduction in the tension force experienced by the eye 30 in the reverse zone C adjacent to the relief zone F.

Referring again to FIG. 2, shown is a schematic representative view of the patient's eyeball 30 with positioned contact lens 32 adjacent to a surface 34 of the eyeball 30. Positioned between the lens 32 and the surface 34 is a tear film layer 36 representing a layer of tear fluid (e.g. comprising lipid, aqueous, and mucin). It is recognised that presence of the tear film layer 36 inhibits adherence of the contact lens 32 to the surface 34, such that adherence is undesirable as it can cause inflammation and scratching of the eyeball due to motion of the contact lens 32 about the surface 34 as the eyeball is moved relative to the eyelid (not shown). As further discussed below, the shape profile (comprised of a number of curve regions 50—see FIGS. 4 and 5—with example widths) of the contact lens 32 provides for areas of positive 37 and negative 38 forces to promote movement 40 of the epithelium tissue of the eyeball 30 to facilitate control of myopia. The positive (push) forces 37 on the epithelium tissue work in conjunction with the negative (pull) forces 38 on the epithelium tissue to promote the movement 40. It is recognised that pressure is defined as the force applied perpendicularly to a surface 34 of the eyeball 30 per unit area of the eyeball 30 (which is therefore proportional to the width w of the respective zone 50, as further provided below). It is through the application of pressure to the eyeball 30 by the lens 32 that myopia is controlled, via the promotion of epithelium tissue movement 40 (e.g. molding of the epithelium tissue to conform towards the shape profile of the lens 32).

Referring to FIGS. 2 and 3 and 4, as such, the lens 32 is designed herein as a reverse geometry lens 32 (RGL) that reforms or molds epithelium tissue through applying both compression and tension forces at different sites across the corneal surface 34 through appropriate design of the width w and curve shape profile of different zones 50 (see FIG. 3). The push-pull balance of the different zones 50 provides for a pull-on of the tissues in the alignment zone D towards the reverse zone C as directed via the relief zone F, as well as push-off of the tissues in the treatment zone (zones A and B), while recognizing that the opposing forces 37,38 generated by the different zones 50 on the corneal tissue are coordinated into proper equilibrium through appropriate selection of design parameters 104 by a user of the lens design tool 102. It is recognised that other forces at work on the corneal tissue include tear film layer 36 fluid forces as well as surface tension forces (e.g. capillary forces) generated by the configuration of the relief curve in the relief zone F. As such, via equilibrium of the forces, the corneal tissue is remolded via the processes of squeeze film forces (referred to as fluid jacket molding) provided by the tension forces 37 as well as through hydrostatic pressure (referred to as vacuum molding), which are exerted via the tear film layer 36 positioned between the lens 32 and the eye surface 34. In general, the curve shape profiles of the different zones 50 act to provide for tension 37 (a pull force on the corneal tissue) and compression 38 (a push force on the corneal tissue) forces of various magnitudes, which are representative and proportional to the thickness of the tear film layer 36. For example, a "steeper" curve profile (for example as provided in the reverse zone C) of the lens 32 generates a tension force 37 transmitted via the tear film layer 36 on the surface 34 of the corneal tissue, recognizing that the steeper the curve (i.e. thicker the tear film layer 36) the greater the tension force 37 generated. On the contrary, a "flatter" curve profile (for example in the middle of zone A near the center of the lens 32 or in the alignment zone D) of the lens 32 generates a compression force 38 transmitted via the tear film layer 36 on the surface 34 of the corneal tissue, recognising that the flatter the curve (i.e. thinner the tear film layer 36) the greater the compression force 38 generated. In general, the sum total magnitude of the compression forces 37 equal the sum total magnitude of the compression forces 38 in order to provide for an equilibrium force lens 32 design.

It is recognised that when the tear film layer 36 in the reverse zone C reaches approximately 60 microns, tiny bubbles or frothing can begin to form in the epithelial tissue, which promotes redistribution of the epithelial tissue. It is has been observed that if the tear film layer 36 exceeds approximately 60 microns, larger bubbles can begin to form, which can create air space that can reduce the hydro-static pressure. Further, once pressure from central zones A+B begins to push tissue into the reverse zone C, the air space decreases thus restoring the pressure. It is recognised that the zones A and B can be considered one zone with one applied curve extending from either side of the apex (point 0,0 in FIG. 4), rather than the two zones A and B having different respective curves, as further discussed below.

In implementation of the herein described lens 32 design, it is desirable to select higher diopter values (e.g. −5 and higher) for even lower levels of diagnosed myopia (e.g. −1 to −3), as typically the lower levels of myopia are associated with initial stages of the disease and thus are more easily controlled (i.e. myopia treatment at the early stages is preferable to inhibit progression of myopia). As such, it is clear that increased tension forces 38 are desirable in the contact lens 32 design, even for lower levels of myopia and therefore the aspheric contact lens 32 design (including a central zone A with applied base eccentricity zone B, a fitting zone or reverse zone C, and a relief zone F—see FIG. 3) is advantageous for all levels of myopia experienced by a person. It is also recognized that proper selection of the width w of the reverse zone B is critical, as too small (i.e. less than 0.6 mm) increases the risk and occurrence of adhesion of the lens 32 to the surface 34 for selected higher diopter values (e.g. −5 and higher). Therefore, the present lens 32 design takes advantage of wider reverse zone C widths w (i.e. greater than 0.5 mm, e.g. 0.6 mm given 0.1 mm increments due to manufacturing tolerances/techniques), while at the same time compensating for inherent reductions in the tension force 38 (as a consequence of the selected wider width w contributing to a proportionately greater unit surface area of tension force application) by application of a base eccentricity curve in the aspheric zone B (or in both Zones A and B) in combination with application of a relief curve in the relief zone F, as further described herein. Further, it is recognised that since the overall dimension of the lens 32 is limited to the size of the person's eyeball 30, selection of a diameter of the central optical zone A+B (e.g. 5.4 mm) should be done in order to provide room for the wider reverse zone C (e.g. 0.6 mm or greater, or otherwise greater than 0.5 mm) along with the additional relief zone F used to create a surface tension force 38 or capillary force in the relief zone F in order to suck/move 40 or otherwise direct the eyeball 30 tissue from an alignment zone D and into/towards the reverse zone C. It is also recognised that using a larger central optical zone A+B (e.g. greater than 5.4 mm) without the application of the base eccentricity curve in the aspheric zone B (or in both Zones A and B) could also cause improper application of the tension force 38 in the vicinity of the edge of the central optical zone A+B (i.e. adjacent to the reverse zone C) and therefore could also contribute to the risk/occurrence of lens adhesion. As such, it is recognized that utilization of a relief zone F and an aspheric zone B (or in both Zones A and B) in the lens 32 design facilitates the proper application of appropriate suction pressure in the reverse zone C (to accommodate the desired maximum correction setting) while at the same time inhibiting adhesion of the lens 32 to the surface 34.

Figure 5:
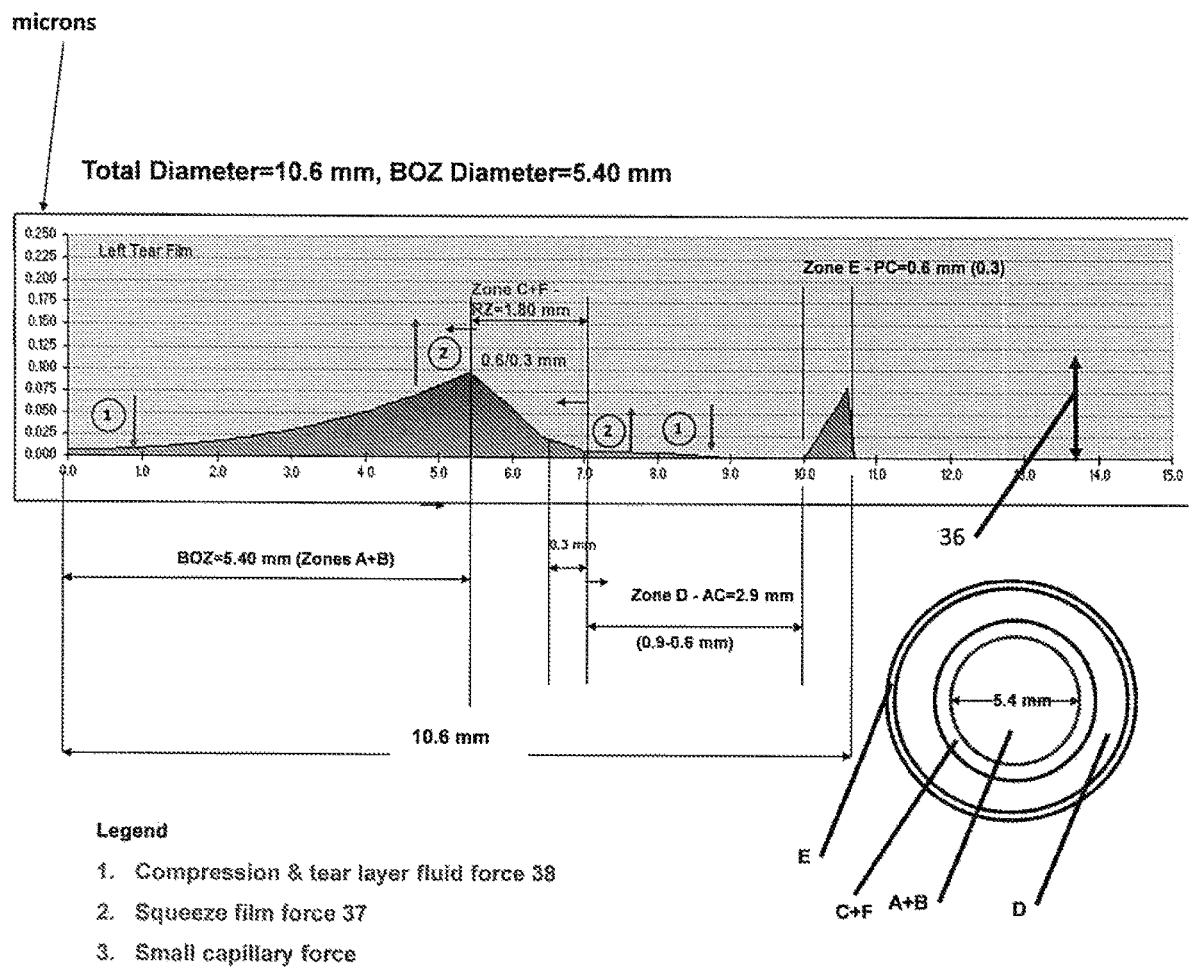
FIG. 5 is shows a further example configuration of the lens of the system of FIG. 1.

Referring to FIGS. 3 and 5, shown is an example contact lens 32 having a plurality of zones 50 of defined width w; namely a back optical zone A, an aspheric zone B, a reverse zone C, a relief zone F, an alignment zone D and a peripheral zone E. It is recognised that zones A and B can be treated as one aspheric zone and thus have only aspheric curve(s) applied to both zones A and B as desired. Each shape profile (i.e. curve) for each of the zones 50 is generated using respective curve profile equations, given by example below. It is recognised that there are shortfalls to achieve a desired result of myopia control. The main reason being many unknowns are involved with curve parameters and their adjustment needed for effective results in control. In order to facilitate myopia control, each individual curve (for each of the zones 50) serves different functions and they are all linked together as a whole entity to provide the desired outcome of myopia control. The following provides a summary of each of the zones 50 and an example respective curve profile equation, such that all zones 50 are listed with their individual function and how they cooperate upon each other to enhance the result (i.e. promote appropriate movement 40 (see FIG. 2) of the epithelium tissue of the eyeball 30 when the contact lens 30 is applied to the surface 34 of the eyeball 32.

Referring to FIG. 4, for example, each of the curve parameters for each of the zones 50 could include 1) a selected curve radius Ri (e.g. the radius of a sphere to one side of the lens 32 such that higher the Ri the flatter the curvature of the lens in the respective zone 50 region and/or the higher the R the steeper the curvature of the lens in the respective zone 50 region), 2) a selected tear film layer thickness 36 (TLTi being the desired distance of the lens 32 material of the zone 50 from the surface 34 of the eye 30 and 3) a selected zone width Wi representing the width of the respective zone 50 as a portion of the total lens width Wt (see FIG. 3). In geometry, the center of curvature of a curve is found at a point that is at a distance from the curve equal to the radius of curvature lying on the normal vector, such that it is the point at infinity if the curvature is zero. A zone 50 of the lens 32 has a center of curvature Ri located in (x, y, z) either along or decentered from a system local optical axis X. The vertex V of the lens surface is located on the local optical axis X. The distance from the vertex V to the center of curvature is the radius of curvature Ri of the lens 32 surface. The sign convention for the optical radius of curvature is as follows: if the vertex V lies to the left of the center of curvature, the radius of curvature Ri is positive. If the vertex V lies to the right of the center of curvature, the radius of curvature Ri is negative. In the case of the RGL lens 32, the radii of curvature Ri are positive.

Zone A

The Back optical zone A containing a base curve is defined as a first portion of the treatment zone related to the pupil size of the eyeball 30. This zone A of the contact lens 32 generates a compression force 37 for flattening of the central cornea of the eyeball 32 and creates a steepening effect of the mid peripheral cornea. An example curve profile for the zone A of a spherical shape is:

1) zone A radius of curvature Ra, 2) zone A width Wa, and zone A tear layer TLTa.

It is recognised that increasing the steepness at the mid peripheral cornea of the eyeball 30 can provide more plus power to facilitate a peripheral myopia defocus result. The steepness can be about 1 to 1.5 times the amount of central flattening. For example, at least 2-3 times steeper than that of central flattening (e.g. with central correction of 4.0D, at 3 mm treatment zone, the plus power generated is about 2.0 diopters D, whilst for 5-6 mm zone, the add can go up to 8-12 diopters D). Hence the amount of mid periphery plus power increases with pupil size (for the treatment zone), however it is recognised that too large a treatment zone can have a diminishing effect of clear central vision. It can be difficult to increase the mid peripheral plus power while maintaining a small treatment zone if we are not targeting extra power at the central zone A (targeting extra power can result in over-correction during the day). Any change in size of zone A can cause a major re-calculation of all other lens 32 parameters. Optimal size has to be used for effective myopia control result but could also consider making room for the rest of the curves 50 (i.e. other than zone A). As discussed above, calculation of the radius Ra can be done using the aspheric equation z(r) provided below, such that both the curves in zone A and zone B are aspheric in nature.

Zone B

A second portion of the treatment zone is the aspheric zone B having a selected base eccentricity ranging from 0.5 to >1.6 (noting the eccentricity of a sphere is defined as zero). Fluid clearance (i.e. tear fill layer 36) in this zone B is important since a zero apical clearance (i.e. zero tear layer thickness) can cause lens 32 decentration which can create lens adhesion & corneal abrasion of the eye surface 34. As such, increasing levels of aspheric in the zone B provide for flattening (i.e. decreasing the radius) of the aspheric curve profile shape as compared to the spherical curve profile shape of in the zone A (i.e. curve radius in zone A is greater than curve radius in zone B).

An example curve profile for the zone B of an aspherical shape is, referring to FIG. 4: 1)

$$z(r) = \frac{r^2}{R\left(1 + \sqrt{1 - (1+\kappa)\frac{r^2}{R^2}}\right)} + \alpha_4 r^4 + \alpha_6 r^6 + \ldots,$$

such that the optic axis in this case lies in the z direction and the z(r) is the sag—the z component of the displacement of the surface from the vertex, at a distance r from the axis. The coefficients describe the deviation of the surface from an axially symmetric quadratic surface specified by R and k. The example curve profile for the zone B (or for zones A and B) would also include zone B width Wb, and zone B tear layer TLTb (or for zones A and B of both aspheric nature also including the zone A width Wa, and zone A tear layer TLTa).

The optical nature of an aspheric lens is such that the aspheric zone B (or zones A and B) creates a small central aperture of distant viewing. The aspheric zone B size of about 1.5 to 3.0 mm diameter (or zones A and B of approximately 5.4 mm), for example. Different from a spherical zone (eccentricity of zero), an aspheric curve provided by the aspheric zone B (or zones A and B) progressively flattens from the central zone A (or from the apex at 0,0) towards the edge of aspheric zone B connected to a reverse zone C adjacent to the aspheric zone B. The effect of positioning the aspheric zone B between the central zone A (or zones A and B) and the reverse zone C creates an effect of progressively diminishing minus power towards the periphery (hence increasing plus power at the reverse zone C and creating a considered high order of spherical aberration). However, one needs to be careful with the application of aspheric zone B (or zones A and B), as it is highly related to the size of the back optical zone A (or zones A and B). For a higher relative asphericity with larger back optic zone A (or zones A and B), the forces generated can be too high/large to create undesired result such as lens 32 binding and adhesion to the surface 34 (see FIG. 2). The contact lens design methodology (as implemented via the program instructions—see FIG. 1) directs the user to the correct asphericity and zone B size based (or zones A and B) on selected parameters as further explained below. Further, the aspheric zone B (or zones A and B) can create even and smooth central applanation (otherwise known as flattening of the convex surface 34) at the center to provide clear vision and inhibit any mixed astigmatism during treatment (i.e. application of the designed lens 32 to the eyeball 30). As such it is recognised that the treatment zone of zones A and B can be provided as aspheric in shape in the lens 32).

Zone C

The reverse zone C is considered the most powerful zone in terms of forces 36,37 generation providing for a negative tear film 36 dynamic. The reverse zone C serves to pile up (i.e. movement 40—see FIG. 2) more corneal tissues of the eyeball 30 from the treatment zone (zones A and B) towards the reverse zone C.

An example curve profile for the zone C shape is:
1) zone C radius of curvature Rc, 2) zone C width Wc, and zone C tear layer TLTc.

The reverse zone C is related to and is responsible for lens 32 steepness and flatness with the force 38 generated (tension and squeeze film force) and is provided as a reciprocal of the curves for zones A and B. In application of the designed lens 32 to the eyeball 30, when tension force (i.e. pressure) increases, the cornea 30 is molded to the back surface of lens 32. If the tear layer thickness (TLT) 36 in the reverse zone C and apical clearance (TLT of the zones A and B) are inaccurate, the cornea 30 tissues cannot accurately mold to the base zone A/B, thereby affecting refractive changes. The tension forces 38 generated in this zone C are largely dependent on the width w (size) of the zone C (see FIG. 2). The narrower the zone C, the larger the force 38 generated and vice versa. Generally speaking, this width w typically dictates the strength of the total permissible forces 37,38 of the lens 32 design.

Bearing the above in mind, the lens 32 design provided herein applies to a width w of the reverse zone C greater than 0.5 mm (e.g. 0.6 mm) as a general rule (the default value), recognizing that any width w less than 0.6 mm (e.g. 0.5 mm or less for 0.1 mm increments) can create undesirable excessive forces 38 of the zone C that can promote adhesion of the lens 32 to the surface 34 (when including the compression force 37 of the base optical zones A and the forces 37 generated in the aspheric zone B (or zones A and B). The value of the forces 37 is adjustable based on the calculation from the computer processor using the reverse zone C equation and other patient/lens parameters supplied by a user of the lens design system 10. If an increased tension force 37 is desired, the amount of base eccentricity of the aspheric zone B (or zones A and B) can be increased to reach the desired results or vice versa. This should satisfy the SAG philosophy. If this curve is too flat, len's SAG is inadequate. If too steep, the len's SAG is too great and the lens 32 could be pushed away from the corneal 30 apex, thereby lessening the molding effect of the epithelium tissue movement 40 (e.g. molding of the epithelium tissue to conform towards the shape profile of the lens 32). Too wide of a zone C could diminish the desired molding effect. The size of the zone C is dependent on the amount of targeting of extra correction of myopia from the original value (i.e. a change in diopter value of the patient eyeball as obtained during myopia diagnosis). Any changes in the curve of this zone C can also change the fitting characteristics of all zones peripheral to it (i.e. the relief zone F and the aspheric zone B). The value of the tear volume in this zone C to create any desired tension force 38 can also depend on the CH, CRF (what are these?) and corneal center thickness (CCC) of the cornea 30. Computer processes will guide the fitter for the best required values. Most of the time, an increase to the force in this zone C is used in order to satisfy the peripheral defocus result desired for myopia control. When the force 37 reaches a level that may cause corneal problems (adhesion & binding), it can then be relieved to some extent to satisfy the tear film equilibrium and to avoid any health problem via application of the relief zone F.

Zone F

The relief zone F can be considered as an enhancement curve. This relief curve is situated in between the reverse zone C and the alignment zone D.

An example curve profile for the zone F shape is:
1) zone F radius of curvature Rf, 2) zone F width Wf, and zone F tear layer TLTf.

Other than providing a reduction in tension forces 38 at the reverse zone C (to relieve some excessive pressure in this zone C at the edges of the zone C), the relief zone F also serves to generate extra forces (small capillary forces and surface tension forces) used to bridge the zones C and D to effectively gather and move 40 corneal tissues from the alignment zone D adjacent to the relief zone F and towards the periphery of the reverse zone C. Finally, the relief zone F also serves to balance the tear force equilibrium between the reverse curve of the reverse zone C and alignment curve of the alignment zone D. The relief curve profile of the relief zone F is an important design consideration in view of the above-discussed functions.

Zone D

The alignment zone D can be comprised of one or more individual alignment curves (e.g. 3), which provide for the overall tightness/looseness fitting of the designed lens 32 with respect to the surface 34.

An example curve profile for the zone D shape is (recognising there can be more than one alignment curve of differing profiles in the alignment zone D):
1) zone D radius of curvature Rd, 2) zone D width Wd, and zone D tear layer TLTd.

The alignment zone can contain the first curve(s) to be determined by the design tool 102, when starting to construct the lens 32, in order to provide for appropriate lens 32 movement and assist in centration during lens 32 wear by the patient. The width(s) w of the alignment zone D curve(s) can be adjusted to optimize room for the other curves in the other zones 50. For example, design tool 102 can provide for the construction of a plurality (e.g. 3) of different the alignment zones D with various radii (i.e. curve profile) and tear film layers. The sizes of the zones D can be designed based on the corneal surface conditions such as the toricity, eccentricity, pressure created by lid tension and positioning. The computer processor of the design tool 102 can help the tool user to determine the proper width w and TLT 36 under the zones D for forces 38 equalization. Compression forces 38 generated at this zone(s) can be lower than those tension forces 37 of the reverse zone C. The computer processor can help to determine the surface tension and capillary forces of this zone(s) D to build up tissues at via movement 40 towards the reverse zone C while facilitating the maintaining of appropriate positioning of the lens 32 while inhibiting adhesion of the underside of the lens 32 to the surface 34 of the eyeball 30. It is recognized that both the reverse and alignment curves satisfy sagittal equivalency in order for the lens 32 to provide for corneal molding during application of the lens 32. It is also recognised that the width of zone D, i.e. Wd, can be used to make room for the desired forces and widths of zones A, B, C, F providing for the majority of the treatment in the treatment zone. In other words, once the curve radius Ri and width parameters Wi have been selected for the zones A, B, C, F, the radius Rd and width Wd for the zone D can be selected in order to balance the desired overall Diameter of the lens 32 (i.e. as dictated by the overall measured dimensions of the patient's eye 30).

Zone E

The peripheral zone E is located at the edge of the lens 32 and as such is the furthest zone 50 from the central optical zone A.

An example curve profile for the zone E shape is:
1) zone E radius of curvature Re, 2) zone E width Wc, and zone E tear layer TLTe.

The peripheral zone E facilitates lens 32 centration. Further, tear meniscus at the edge of lens 32, when in contact with air, can produce a negative or tension force 38. Accordingly, the curve of the peripheral zone E serves to control excessive lens adherence to corneal surface for lens centration. Proper calculation (via the computer processor using the peripheral zone curve) determines the amount of tear reservoir available to move under the lens 32, and to facilitate tear continuity and flow under the lens 32 surface. As long as the TLT 36 under the lens 32 inside the peripheral zone E is sufficient and balanced, a seal-off lens can enhance centration.

It is recognised in the above that a radius of curvature Ri is chosen for each of the zones A, B, C, D, E, F however it is recognised that more complex curve shapes (e.g. having multiple or variations on a single radius) can be substituted as desired.

In view of the above, all zones 50 have to work together in order to have a construction of the lens 32 with balanced forces 37,38 for effective result of the corneal molding. The computer processor can provide for calculations for this purpose via usage of the appropriate curve(s) profile shape assigned to each zone 50. As such, given the above, it is recognised that contact lens 32 size is dictated by the size of the person's eyeball 30, thereby for myopia control the available area for treatment, i.e. location of suction forces 38, is dictated by the overall size of the treatment zones A, B, C, F which leaves available space for the rest of the required zones (e.g. alignment D, peripheral E). It is also recognised that the strength (i.e. steepness) of the reverse curve of the reverse zone C provides for the suction or tension force 38 applied to the eyeball 32 of the person in the reverse zone C, for a given base curve of the central optical zone A (providing the compression force 38) and a given alignment curve of the alignment zone D (providing for maintaining positioning or alignment of the lens 32 on the eyeball 30). As such, the width w of the reverse zone C typically dictates the strength of the tension force 37 permissible, such that narrower widths w (e.g. less than 0.6 mm such as 0.5 mm) result in the creation of increased tension forces 37 for a given reverse curve shape. As provided below, an alternative to using narrow width reverse zones C (i.e. less than 0.6 mm) to generate increased tension forces 37, the present design tool uses wider reverse zones C (e.g. 0.6 mm or greater tending to decrease/lower the tension force 37) which is then compensated for by 1) the application of a base eccentricity curve shape of the aspheric zone B to the base curve shape in the central zone A (or for both zones A and B) adjacent to the reverse zone C and 2) the addition of the relief zone F with relief curve shape situated between the reverse zone C and the alignment zone D. The contribution of the application of the base eccentricity curve shape (e.g. of both zones A and B) is to increase the tension force 37 generated by the reverse curve via the introduction of the aspheric nature to the base curve shape (which can be spherical in nature). At the same time, the addition of the relief zone F with associated relief curve shape provides for a reduction in the tension force 37 experienced by the eyeball 30 in the reverse zone D region adjacent to the relief zone F, thereby assisting in the inhibition of adhesion of the lens 32 to the surface 34.

Finally, this lens design tool 102 can also help to modify the fitting condition to allow the lens 30 to sit properly on the eyeball surface 34, and to reach equilibrium. You can evaluate a fitting correlation between the cornea 30 and the contact lens 32 by the sagittal depth (sag) correlation between the cornea 30 and the contact lens 32. In a contact lens 32, sag defined as a perpendicular line from the apex of the lens 32 to a line intersecting the diameter of the lens 32. The goal of custom lens 32 fitting is the proper alignment of the posterior lens 32 surface to the surface 34 of the cornea 30. This is what normally called Lens SAG equilibrium and is important for lens 30 construction based on the design. For the custom designed lens 32 of FIG. 2, Lens sag can be defined as the sagittal height of each of the individual zones 50 of the lens 32 added together. The sag of the lens 32 is equal to the sag of the zones A+B radius/sag zones A+B diameter (R of A+B)/(D of A+B), plus the sag of the reverse zone C over its width, and plus the sag of the alignment zone D. The sag of the lens 32 can be measured to the diameter that represents the common chord of contact between the lens 32 and the corneal surface 34.

Referring to FIGS. 7, 8, 9 shown is an example operation of the system 10 of FIG. 1. At step 150, the machine 110 takes measurements of the eye 30 parameters 104 (e.g. obtain measurement of one or more biomechanical properties of the cornea). At step 152, the preference parameters 104 can be input by the doctor based on patient data (e.g. measured eye diameter) such as desired lens diameter (related to corneal diameter measurement), maximum corrective power (e.g. −6.5 for a measured −4 Diopter reading of the patient eye(s) 30 as an obtained measurement for degree refractive error of the eye 30 in diopters), base TLT for the apex in zone A (e.g. apical TLT) based on strength of the correction (e.g. higher corrections can dictate larger apical TLT), base curve eccentricity (as dictated by the measured Eccentricity in FIG. 8) such that an increase in base curve eccentricity results in an increase in aspheric shape of zone B (or zones A and B) and thus an increase in respective forces 37,38 in the zones A and B (and C and F for balancing reverse and relief curves). As noted, a default value of Reverse Curve Width of 0.6 (e.g. greater than 0.5 mm) can be maintained or changed as desired.

At step 154, the software tool 102, via the computer processor 108 (see FIG. 1) can calculate the radii of the various curves for the zones A, B, C, D, E, F as noted above, based on the selected parameters 104 (e.g. base curve eccentricity, Optical Zone, Apical TLT, etc.). It is recognised that for various widths Wi not actively selected by the physician (e.g. user of the tool 102), the software tool 102 can provide default values retrieved from memory 114). It is also recognised that the preference parameters 104 can be input before or after calculation of the widths Wi and curve radii Ri is performed, for example in an iterative fashion as the user fine tunes the lens 32 design using the provided default values and adjustable values of the tool 102 in order to design the lens 32 abiding by the overall lens diameter (dictated by the actual eye size), the degree of correction required (dictated by the measured patient prescription and K readings), as well as the measured Eccentricity of the eye, recognizing that each lens 32 for each eye 30 of the patient can have different lens designs due to differing parameter 104 measurements. At this step the user can define/select a diameter of the central zone of the contact lens 32 based on pupil size, the diameter being equal to or less than 5.4 mm as part of the overall lens diameter Wt. At this step the user can define/select a diameter of the central zone of the contact lens 32 based on pupil size, the diameter being equal to or less than 5.5 mm as part of the overall lens diameter Wt. At this step the user can define/select a diameter of the central zone of the contact lens 32 based on pupil size, the diameter being equal to or less than 5.6 mm as part of the overall lens diameter Wt. At this step the user can define/select a diameter of the central zone of the contact lens 32 based on pupil size, the diameter being equal to or less than 5.7 mm as part of the overall lens diameter Wt.

Also shown in FIG. 9 is the Target Lens Power of 2.00 (by example, which is referred to by a person skilled in the art as the Jesson factor. Referring to FIG. 8, the sphere measurement is the measure prescription (e.g. Rx), the Eccentricity (e. 0.25) is the actual measured aspheric shape of the patient's eye 30 (recognizing an eccentricity of 0 would denote a spherical shape hence no aspheric nature), the Cylinder represents a measurement of astigmatism of the eye 30 and Axis represents the axis measurement of the astigmatism.

As part of step 154, the executable instructions can be used to facilitate the method for generating the aspheric contact lens design 120 for facilitating myopia control of the cornea of the patient by selecting a base curve profile and width for the central zone (e.g. zones A and B) based on the refractive error and the one or more biomechanical properties, the base curve profile defining a compression force strength on the cornea when the contact lens is positioned on the eye, the base curve profile including a central zone tear layer thickness TLT and a central zone radius of curvature R; define a width Wr of a reverse zone C adjacent to and encircling the central zone A, B, the width being greater than 0.5 mm; select a reverse curve profile for the reverse zone C compatible with the base curve profile, the reverse curve profile defining a tension force strength on the cornea when the contact lens 32 is positioned on the eye 30, the reverse curve profile including a reverse zone tear layer thickness TLTr and a reverse zone radius of curvature Rr; modify the base curve profile adjacent to the reverse zone C by applying a selected base eccentricity curve profile for enhancing the tension force strength of the reverse zone C, said applying contributing to the aspheric nature of the contact lens 30, the base eccentricity curve profile including an aspheric zone tear layer thickness TLT and an aspheric zone base eccentricity in the zone(s) A, B; define a width Wf of a relief zone F of the contact lens 32 adjacent to and encircling the reverse zone c; and select a relief curve profile for the relief zone F, the relief curve profile moderating the tension force strength adjacent to the relief zone F, the relief curve profile including a relief zone tear layer thickness TLTf and a relief zone radius of curvature Rf. It is recognised that the pressure exerted in the corneal tissue in zone F is less than the pressure in zone C and greater than the pressure in zone D.

It is recognised that the software tool 102 calculates the lens design (e.g. zone width Wi, TLTi, radii Ri) based on the base curve eccentricity (affecting zones A, B) and other parameters 104 (e.g. overall lens width Wt, maximum correction, etc), recognizing that selecting an increase from the given/current/default value of the design (e.g. TLTi, radii Ri) typically results in an increase in the forces generated for that respective zone 50. Conversely, an increase in the zone width Wi from the given/current/default value of the lens design would result in a decrease in the forces generated for that respective zone 50, which if not desired as such, would provide for a change as increase in the TLTi and/or radius Ri of that zone to compensate (i.e. reraise the forces that were decreased via the increased change in width Wi of the zone 50).

It is recognised that the software tool 102 calculates the lens design (e.g. zone width Wi, TLTi, radii Ri) based on the base curve eccentricity (affecting zones A, B) and other parameters 104 (e.g. overall lens width Wt, maximum correction, etc), recognizing that selecting an decrease from the given/current/default value of the design (e.g. TLTi, radii Ri) typically results in a decrease in the forces generated for that respective zone 50. Conversely, a decrease in the zone width Wi from the given/current/default value of the lens design would result in an increase in the forces generated for that respective zone 50, which if not desired as such, would provide for a change as a decrease in the TLTi and/or radius Ri of that zone to compensate (i.e. lower the forces that were increased via the decreased change in width Wi of the zone 50).

In view the above, it is recognised that selection of any of the parameters 104 via the tool 102 that results in a desired increase in the forces for a particular zone 50 would not have to be compensated for by selection of other parameters 104 in order to correspondingly lower the raised force(s). Further, in view the above, it is recognised that selection of any of the parameters 104 via the tool 102 that results in a desired decrease in the forces for a particular zone 50 would not have to be compensated for by selection of other parameters 104 in order to correspondingly increase the raised force(s). Accordingly, one should recognize the interdependence of the parameters 104 and thus their influence on the forces for a given zone 50 as well as their influence on the forces design for adjacent zones 50 of the lens 32. For example, increases in the prescription Rx (e.g. raising the maximum correction force of the lens 32) typically results in a widening of the relief zone width Wf along with an increase in the TLTf of the zone F in order to facilitate an increase in gathering of corneal tissue from the alignment zone D while at the same time helping to inhibit adhesion of the lens 32 to the surface 34 of the eye 30 due to forces 37,38 present in the zones A, B, C reflecting the desired maximum correction power. It is also recognised that based on the pressure generated by the forces in the zone F, the magnitude of the pressure in the zone D (generated by the force resulting from the selection of Rd, Wd, TLTd) could be adjusted such that the pressure in zone D is always less than the pressure in zone F. It is also recognised that the pressure generated in zone D can be provided by section of the parameters Rd, Wd, TLTd such that suction forces are present to promote gathering of the corneal tissue from the alignment zone D and towards the relief zone F while at the same time inhibiting adhesion of the lens 32 in the vicinity of the zone D to the eye surface 34, recognizing if the suction forces in zone D are below a set D gathering threshold then the desired gathering of corneal tissue would be negligible while if the suction forces in zone D are below a set D adhesion threshold then the lens is prone to adhesion during wear.

At step 156, the alignment zone D can be adjusted in order to account for the selected curve profiles of zones A, B, C, F, recognising that zone D facilitates both alignment of the lens 32 on the eye 30 as well as facilitating gathering of corneal tissue from the alignment zone D towards the reverse zone C (via the relief zone F) due to requisite suction forces provided by the curve D profile. For example, define a width of the alignment zone D of the contact lens 32 adjacent to and encircling the relief zone F in order to equate the Lens diameter Wt equal to the selected diameter (e.g. reducing the alignment zone width Wd in order to match the selected lens diameter or increasing the alignment zone width Wd in order to match the selected lens diameter); and select the alignment curve profile for the alignment zone D, the alignment curve profile including an alignment zone tear layer thickness TLTd and an alignment zone radius of curvature Rd. It is recognised that that the TLTd as well as the radius Rd can be adjusted in order to provide for an appropriate level of suction forces 37—see FIG. 2—in this zone D, recognising that too great a suction force can result in adhesion of the lens 32 to the eye surface 34 while too low a suction force (below a set D gathering threshold) can result in an undesirable magnitude of movement of the lens 32 when applied to the eye 30 and/or a loss in ability to gather corneal tissue towards the relief zone F. It is recognised that as well, the TLTi of the various zones can be adjusted, such that a greater TLTi than the current setting results in a larger separation distance of the lens 32 from the corneal surface 34 and/or a greater force provided for in the respective zone 50 than the current setting. In general it is recognized that as the magnitude of the width Wc of the reverse zone C is raised above 0.5 mm, the greater the base curve eccentricity that must be applied to the curve profile (e.g. radius) in zones B or A and B, in order to provide for the maximum correction as specified in the parameters 104.

At step 158, the user can define or otherwise confirm the width Wc of the peripheral zone E of the contact lens 32 adjacent to and encircling the alignment zone D and select a peripheral curve profile for the peripheral zone E such that the peripheral curve profile includes a peripheral zone tear layer thickness TLTe and a peripheral zone radius of curvature Re.

At step 160, the parameters 104 can be adjusted in order to recalculate the curve profiles including the radii Ri, the widths Wi and the TLTi of the zones A, B, C, D, E, F in order to balance the forces 37,38 to provide for the desired maximum corrective power (via forces generated by the zones A, B, C, F) as well as providing for appropriate positioning and alignment of the lens 32 (via forces gener- ated in zone D) as well as providing for appropriate peripheral forces in zone E. Once one or more of the parameters 104 are readjusted, any or all of steps 152 5 158 can be repeated buy the software tool 102. For example, one of the adjusted parameters could be the reverse zone width Wr, thus resulting in a lowering of the forces in the reverse zone C for the given TLT r and radius Rr and thus require an adjustment in zones A and/or B (e.g. increase in the base curve eccentricity in zones A and/or B, an increase in the TLTa and/or TLTb) and/or an adjustment in the reverse zone C (e.g. increase in the TLTr and/or steeper radius Rr), in order to provide for the desired maximum correction power as specified in the parameters 104 (see FIG. 9—e.g. −6.5). It is also recognised that as a consequence of adjustment, the width Wf of the relief zone F could be adjusted (e.g. made wider than the current setting, made narrower than the current setting) as well as the width Wd of the alignment zone could be adjusted (e.g. made wider than the current setting, made narrower than the current setting). It is also recognised that as a consequence of adjustment, the width TLTf of the relief zone F could be adjusted (e.g. made taller than the current setting, made shorter than the current setting) as well as the TLTd of the alignment zone Wd could be adjusted (e.g. made taller than the current setting, made shorter than the current setting). Once completed, i.e. the parameters 104 are finalized, the lens design is output at step 162 for use in manufacture of the physical lens by a lens making machine according to the calculated cure profiles as noted above.

Referring to FIG. 8, the software tool 102 can provide via the user interface 112 (see FIG. 1) various controls 105 for adjusting the parameters 104, e.g. making the radii of selected zones 50 (see FIG. 3) either progressively steeper or flatter, recognising that steeper results in an increase in the respective zone 50 force 37,38 while flatter results in a decrease in the respective zone 50 force 37,38. It is recognised that the adjustments can be made separately for the Right and Left eye lenses 32.

Further, the above steps can include the at least one biomechanical property 104 is selected from the group consisting of central thickness, hysteresis and rigidity of the cornea. Further, the above steps can include adjusting the reverse curve profile to account for the at least one biomechanical property. Further, the above steps can include the alignment curve profile is selected before the reverse curve profile. Further, the above steps can include the alignment curve profile is selected after the reverse curve profile. Further, the above steps can include adjusting at least one of the reverse curve profile, the relief curve profile or the alignment curve profile such that the pressure exerted in the reverse zone is greater than the pressure exerted in the relief zone which is greater than the pressure exerted in the alignment zone to facilitate gathering of corneal tissue from the alignment and relief zones towards the reverse zone.

It is recognized that the steps provided above with regard to FIGS. 7, 8, 9 can be programmed into the machine 110 having measurement devices 111 for measuring the eye surface geometry as well as the biomechanical properties 104, in order to provide for an integrated machine of eye measurement and lens design. As such, the computing device 101 of FIG. 1 can include the machine 110, as an integrated device and/or as separate devices coupled together to provide for an end to end solution of eye measurement and resulting lens 32 design 120 based on the measured parameters 104. As such, the machine 110 would be coupled to or otherwise have respective processor(s) 108, user interface 112, device infrastructure 116 executable instructions (e.g. for implementing the method described herein of lens 32 design as well as for performing measurement and recording via storage 114 of the eye parameters 104) as well as memory 114. It is recognized that user of the device 100,110 would be facilitated via the measurements 104 and the design parameters 104 of the software tool 102 to take measurements of a patient's eyes 30 and then design appropriate lens 32 to provide during wearing of the lenses 32 the compression force strength and the tension force strength of the contact lenses to reshape corneal curvature in a mid-peripheral region of the patient's eyes 30 to address the myopia control.

Referring again to FIG. 1, the computer device 100 can comprises a land-based network-enabled personal computer. However, the invention is not limited for use with personal computers. For instance, one or more of the network devices 100 can comprise a wireless communications device, such as a wireless-enabled personal data assistant, a tablet, or e-mail-enabled mobile telephone if a network is configured to facilitate wireless data communication. The computer device 100 can include the network connection interface 118, such as a network interface card or a modem, coupled to the device infrastructure 116. The connection interface 118 can be connectable during operation of the computer device 100 to a network (e.g. an intranet and/or an extranet such as the Internet), which enables the devices to communicate with other computer devices as appropriate. The computer device 100 can also have the user interface 112, coupled to the device infrastructure 116, to interact with a user (e.g. optometrist—not shown). The user interface 112 can include one or more user input devices such as but not limited to a QWERTY keyboard, a keypad, a stylus, a mouse, a microphone and the user output device such as an LCD screen display and/or a speaker. If the screen is touch sensitive, then the display can also be used as the user input device as controlled by the device infrastructure 116. Operation of the computer device 100 is facilitated by the device infrastructure 116. The device infrastructure 116 includes one or more computer processors 108 and can include an associated memory (e.g. a random access memory 114). The computer processor 108 facilitates performance of the computer device 100 configured for the intended task (e.g. of the respective module(s) of the design tool 102) through operation of the network interface 118, the user interface 112 and other application programs/hardware of the computer device 100 by executing task related instructions associated with lens 32 design. These task related instructions can be provided by an operating system, and/or software applications located in the memory, and/or by operability that is configured into the electronic/digital circuitry of the processor(s) 108 designed to perform the specific task(s). Further, it is recognized that the device infrastructure 116 can include a computer readable storage medium 114 coupled to the processor 108 for providing instructions to the processor 108 and/or to load/update the instructions. The computer readable medium 114 can include hardware and/or software such as, by way of example only, magnetic disks, magnetic tape, optically readable medium such as CD/DVD ROMS, and memory cards. In each case, the computer readable medium 114 may take the form of a small disk, floppy diskette, cassette, hard disk drive, solid-state memory card, or RAM provided in the memory module 114. It should be noted that the above listed example computer readable mediums 114 can be used either alone or in combination.

Further, it is recognized that the computer device 100 can include executable applications (such as the design tool 102) comprising code or machine readable instructions for implementing predetermined functions/operations including those of an operating system and lens design modules, for example. The processor 108 as used herein is a configured device and/or set of machine-readable instructions for performing operations as described by example above. As used herein, the processor 108 can comprise any one or combination of, hardware, firmware, and/or software. The processor 108 acts upon information by manipulating, analyzing, modifying, converting or transmitting information for use by an executable procedure or an information device, and/or by routing the information with respect to an output device. The processor 108 may use or comprise the capabilities of a controller or microprocessor, for example. Accordingly, any of the functionality of the design tool 102 can be implemented in hardware, software or a combination of both. Accordingly, the use of a processor 108 as a device and/or as a set of machine-readable instructions is hereafter referred to generically as a processor/module for sake of simplicity. Further, it is recognised that the design tool 102 can include one or more of the computer devices 100 (comprising hardware and/or software) for implementing the lens design method, as desired.

In view of the above descriptions of storage, the storage 114 can be configured as keeping the stored data (e.g. predefined curve shape profiles, predefined tear layer thicknesses for each of the zones 50 as selectable by the user) in order and the principal (or only) operations on the stored data are the addition of and removal of the stored data from the storage (e.g. FIFO, FIAO, etc.). For example, the storage can be a linear data structure for containing and subsequent accessing of the stored data and/or can be a non-linear data structure for containing and subsequent accessing of the stored data. Further, the storage receives various entities such as data that are stored and held to be processed later. In these contexts, the storage can perform the function of a buffer, which is a region of memory used to temporarily hold data while it is being moved from one place to another. Typically, the data is stored in the memory when moving the data between processes within/between one or more computers. It is recognised that the storage can be implemented in hardware, software, or a combination thereof. The storage is used in the design system 10 when there is a difference between the rate/time at which data is received and the rate/time at which the data can be processed.

Further, it will be understood by a person skilled in the art that the memory/storage described herein is the place where data can be held in an electromagnetic or optical form for access by the computer processors/modules. There can be two general usages: first, memory is frequently used to mean the devices and data connected to the computer through input/output operations such as hard disk and tape systems and other forms of storage not including computer memory and other in-computer storage. Second, in a more formal usage, memory/storage has been divided into: (1) primary storage, which holds data in memory (sometimes called random access memory or RAM) and other "built-in" devices such as the processor's L1 cache, and (2) secondary storage, which holds data on hard disks, tapes, and other devices requiring input/output operations. Primary storage can be faster to access than secondary storage because of the proximity of the storage to the processor or because of the nature of the storage devices. On the other hand, secondary storage can hold much more data than primary storage. In addition to RAM, primary storage includes read-only memory (ROM) and L1 and L2 cache memory. In addition to hard disks, secondary storage includes a range of device types and technologies, including diskettes, Zip drives, redundant array of independent disks (RAID) systems, and holographic storage. Devices that hold storage are collectively known as storage media.

I claim:

1. A method for generating an aspheric contact lens design for facilitating myopia control of a cornea of a patient, the method stored as a set of instructions in memory for execution by a computer processor to:
   select a base curve profile for a central zone based on refractive error and one or more biomechanical properties of an eye of the patient, the base curve profile defining a compression force strength on the cornea when the contact lens is positioned on the eye, the base curve profile including a central zone tear layer thickness and a central zone radius of curvature;
   define a width of a reverse zone adjacent to and encircling the central zone;
   select a reverse curve profile for the reverse zone compatible with the base curve profile, the reverse curve profile defining a tension force strength on the cornea when the contact lens is positioned on the eye, the reverse curve profile including a reverse zone tear layer thickness and a reverse zone radius of curvature;
   modify the base curve profile adjacent to the reverse zone by applying a selected base eccentricity curve profile for enhancing the tension force strength of the reverse zone, said applying contributing to the aspheric nature of the contact lens, the base eccentricity curve profile including an aspheric zone tear layer thickness and an aspheric zone base eccentricity;
   wherein the compression force strength and the tension force strength of the contact lens cooperate to reshape corneal curvature in a mid-peripheral region to address the myopia control when the contact lens is applied to the eye.

2. The method of claim 1 further comprising to: define a width of a relief zone of the contact lens; and
   select a relief curve profile for the relief zone, the relief curve profile moderating the tension force strength, the relief curve profile including a relief zone tear layer thickness and a relief zone radius of curvature.

3. The method of claim 2 further comprising to: define a width of an alignment zone of the contact lens adjacent to and encircling the relief zone.

4. The method of claim 2, wherein the relief zone is between the reverse zone and an alignment zone such that the relief zone is adjacent to and encircling the reverse zone.

5. The method of claim 1, wherein the compression force strength facilitates application of a squeeze film push force on tissue of the cornea, the base curve profile providing flattening of the central zone towards the reverse zone.

6. The method of claim 2 further comprising adjusting at least one of the reverse curve profile or the relief curve profile such that the pressure exerted in the reverse zone is greater than the pressure exerted in the relief zone to facilitate gathering of corneal tissue from an alignment zone and the relief zone towards the reverse zone.

7. The method of claim 1 further comprising to adjust the reverse curve profile to account for the at least one biomechanical property.

8. The method of claim 4, wherein the alignment curve profile of the alignment zone is selected after the reverse curve profile.

9. The method of claim 1 further comprising positioning an aspheric zone between the central zone and the reverse zone in order to facilitate an effect of progressively diminishing minus power towards a periphery of the lens, wherein said progressively diminishing provides for increasing plus power at the reverse zone and a higher order of spherical aberration, wherein the central zone is a back optical zone.

10. The method of claim 3, wherein the relief zone serves to generate extra forces used to bridge the alignment zone and the reverse zone to effectively gather and move corneal tissues from the alignment zone adjacent to the relief zone f and towards a periphery of the reverse zone.

11. The method of claim 1, wherein a width of the reverse zone is greater than 0.5 mm.

12. The method of claim 1, wherein via equilibrium of the forces corneal tissue is remolded using a processes of squeeze film forces provided by the tension force as well as through hydrostatic pressure, which are exerted via the tear film layer in the reverse zone, the tear film layer positioned between the lens and a surface of the eye.

13. The method of claim 12, wherein the tear film layer in the reverse zone is less than 60 microns in order to inhibit the formation of bubbles which can create air space that can reduce the hydro-static pressure.

14. The method of claim 9, wherein utilization of a relief zone and the aspheric zone facilitates application of suction pressure in the reverse zone in order to accommodate a desired correction setting while at the same time inhibiting adhesion of the lens to a surface of the eye.

15. A lens design machine for generating an aspheric contact lens design for facilitating myopia control of a cornea of an eye of a patient, the machine including:
   a measurement device for obtaining measurement for a degree of refractive error of the eye and for obtaining measurement of one or more biomechanical properties of the cornea;
   a computer processor and memory having a stored as a set of instructions for execution by a computer processor to:
   select a base curve profile for a central zone based on the refractive error and the one or more biomechanical properties of an eye of the patient, the base curve profile defining a compression force strength on the cornea when the contact lens is positioned on the eye, the base curve profile including a central zone tear layer thickness and a central zone radius of curvature;
   define a width of a reverse zone adjacent to and encircling the central zone;
   select a reverse curve profile for the reverse zone compatible with the base curve profile, the reverse curve profile defining a tension force strength on the cornea when the contact lens is positioned on the eye, the reverse curve profile including a reverse zone tear layer thickness and a reverse zone radius of curvature;
   modify the base curve profile adjacent to the reverse zone by applying a selected base eccentricity curve profile for enhancing the tension force strength of the reverse zone, said applying contributing to the aspheric nature of the contact lens, the base eccentricity curve profile including an aspheric zone tear layer thickness and an aspheric zone base eccentricity;
   wherein the compression force strength and the tension force strength of the contact lens cooperate to reshape corneal curvature in a mid-peripheral region to address the myopia control when the contact lens is applied to the eye.

16. An aspheric contact lens for facilitating myopia control of a cornea of an eye of a patient, the contact lens including:
   a base curve profile for a central zone based on the refractive error and the one or more biomechanical properties of an eye of the patient, the base curve profile defining a compression force strength on the cornea when the contact lens is positioned on the eye, the base curve profile including a central zone tear layer thickness and a central zone radius of curvature;

a width of a reverse zone adjacent to and encircling the central zone;

a reverse curve profile for the reverse zone compatible with the base curve profile, the reverse curve profile defining a tension force strength on the cornea when the contact lens is positioned on the eye, the reverse curve profile including a reverse zone tear layer thickness and a reverse zone radius of curvature;

a modification of the base curve profile adjacent to the reverse zone including an applied selected base eccentricity curve profile for enhancing the tension force strength of the reverse zone, the selected base eccentricity curve profile contributing to the aspheric nature of the contact lens, the selected base eccentricity curve profile including an aspheric zone tear layer thickness and an aspheric zone base eccentricity;

wherein the compression force strength and the tension force strength of the contact lens cooperate to reshape corneal curvature in a mid-peripheral region to address the myopia control when the contact lens is applied to the eye.

* * * * *